United States Patent [19]

Gordon

[11] 4,344,932

[45] Aug. 17, 1982

[54] NAIL CLEANSER

[75] Inventor: Harry W. Gordon, New York, N.Y.

[73] Assignee: Del Laboratories, Inc., Farmingdale, N.Y.

[21] Appl. No.: 155,607

[22] Filed: Jun. 2, 1980

[51] Int. Cl.³ .............................................. A61K 7/04
[52] U.S. Cl. ........................................ 424/61; 132/73
[58] Field of Search ........................... 132/73; 424/61; 252/542, 544, 153

[56] References Cited

U.S. PATENT DOCUMENTS

| | | | |
|---|---|---|---|
| 2,268,642 | 1/1942 | Carter | 424/61 X |
| 2,764,168 | 9/1956 | Herz | 132/73 |
| 3,150,048 | 9/1964 | Hollab | 424/61 |
| 3,384,592 | 5/1968 | Weems | 424/61 |
| 3,441,645 | 4/1969 | McKissick | 424/61 |
| 3,483,008 | 12/1969 | Herr | 424/61 X |
| 3,483,289 | 12/1969 | Michaelson | 424/61 |

*Primary Examiner*—G. E. McNeill
*Attorney, Agent, or Firm*—Kirschstein, Kirschstein, Ottinger & Cobrin

[57] ABSTRACT

A nail cleanser containing sodium ethylenediamine tetraacetic acid, urea and water. When applied to nails it removes various stains such as tobacco, nail pigment, shoe polish, furniture polish and hair dyes.

7 Claims, No Drawings

NAIL CLEANSER

BACKGROUND OF THE INVENTION

1. Field of the Invention

A nail cleanser for nails on the human hand for the purpose of removing various types of stains.

2. Description of the Prior Art

Nails are a prideful accouterment of American females. They assiduously file, shape, buff, oil and polish them in order to make them attractive. However, the appearance of nails is frequently spoiled by the presence of stains. This, of course, is particularly true where a clear polish is used or no polish at all is applied. Nails are notoriously porous and become more so with advancing age. This porousity increases their tendency to readily stain. The stains come from various sources. A primary source is nicotine from handling lighted cigarettes. Nails also pick up stains from various chemicals that are handled by women in their homes and occupations. In addition, nails yellow with age. This is believed to be caused by melamine, a brown pigment synthesized in the body by normal biological processes and carried up into the nails from the nail beds. Sometimes the stains appear as spots and sometimes as an overall coloration which permeates the nails or upon occasion only is present at the outer surfaces of the nails. It would be most desirable to remove such stains but to date no satisfactory cosmetic stain remover has been marketed, to the best of applicant's knowledge. The only relevant material that has been observed is an article in the Chemical Formulary of 1951 at volume IX page 91 where various bleaches are disclosed for finger nails. These, however, are not general purpose nail cleansers. Applicant also is aware of the following patents which disclose compositions including some of the chemical ingredients of the instant nail cleanser. However, the components are not used in the correct proportions for nail cleansing and indeed include many other chemical ingredients, all for purposes other than that of removing stains:

U.S. Pat. No. 3,694,366
U.S. Pat. No. 3,708,437
U.S. Pat. No. 3,957,967
U.S. Pat. No. 4,115,293

SUMMARY OF THE INVENTION

Purpose of the Invention

It is an object of the invention to provide a nail cleansing composition of the character described which is simple and inexpensive and which upon application to the nails and removal within a short period of time will remove stains.

It is another object of the invention to provide a nail cleanser of the character described which is easy to use and requires no special instructions for its application.

It is another object of the invention to provide a nail cleanser of the character described which leaves the nails in good condition to receive subsequent application of nail cosmetics such for instance as clear or opaque nail polishes.

It is another object of the invention to provide a nail cleanser of the character described which has no detrimental effects on the nails, the cuticles or the adjacent skin.

It is another object of the invention to provide a nail cleanser of the character described which is non-allergenic and non-toxic.

It is another object of the invention to provide a nail cleanser of the character described which includes chelating agents as necessary ingredients and which further includes conventional cosmetic additives such as thickeners, preservatives, texturizing agents and abrasives.

It is another object of the invention to provide a nail cleanser of the character described which does not include among its ingredients any unstable or potentially explosive chemicals such as oxidizers.

Other objects of the invention in part will be obvious and in part will be pointed out hereinafter.

BRIEF DESCRIPTION OF THE INVENTION

The nail cleanser of the present invention is characterized by the inclusion of essential ingredients present within prescribed critical ranges, by the further necessary inclusion of a liquid carrier for these ingredients and by the optional inclusion of various additives whose presence, although desirable for maximum efficiency of the cleanser, for ease of use and for various cosmetic and odoriferous purposes, is not essential. The necessary ingredients are: Firstly, a particularly effective chelating agent and secondly a chemical which is a milder chelating agent and desirably also is a solubilizing agent. Specifically the first chelating agent, i.e. the one having the higher effectiveness, is selected from a group consisting of ethylenediamine tetraacetic acid, phytol, phytic acid, nitrilo-triacetic acid, diethylene triamino pentaacetic acid, sodium tripolyphosphates and metaphosphate, sodium hexamethaphosphate, trisodium phosphate and ethylene diamino tetraacetic acid. The preferred first chelating agent is an alkali metal salt of ethylenediamine tetraacetic acid, for example sodium ethylenediamine tetraacetic acid. For the second, i.e. milder, chelating agent urea is employed or a substitute therefor, such as allantoin, penthenol and aloe vera extract.

Although the present invention is not to be so limited it is believed that the new cleansing agent acts on stains in nails by complexing the metal ions that are present in most stains and thereby rendering the stain leuco, i.e. colorless. The metal ions thus extracted become solubilized by the chelating agent and thereupon form a soluble ingredient of the cleansing agent. Subsequently they leave the nail with the cleansing agent when the cleansing agent is removed. The second, i.e. milder, chelating agent is believed to assist in the extraction and solubilization of the metal ions and in general to exert a solubilizing effect on organic staining material so as to aid in removing it from the nails.

The liquid carrier is of course a necessary ingredient. Various liquid carriers can be used and desirably they are such that the first and second necessary ingredients are soluble or dispersible and suspendable therein. Typical acceptable liquid carriers are water, liquid alcohols and acetone. In general the liquid carrier desirably is inexpensive and water therefore is the carrier of choice.

The critical range for the first chelating agent is from about 1 percent to about 30 percent by weight of the nail cleanser. The critical range for the second chelating agent is from about 1 percent to about 30 percent by weight of the nail cleanser. The critical range for the liquid carrier is from about 40 percent to about 80 percent by weight of the nail cleanser. The preferred ranges for these three constituents are: for the first chelating agent about 1 percent to about 3 percent, for the second chelating agent from about 4 percent to about 6 percent and for the liquid carrier from about 70 percent to about 80 percent of the cleanser.

The foregoing three constituents are the constituents of which the liquid carrier essentially consists.

In addition to the essential constituents there are as mentioned earlier a number of desirable additives, for example a mild abrasive such as silica, diatomaceous earth and talc in an amount up to about 5 percent, preferably from about 1 to about 3 percent of the cleanser, to improve the texture hydrolized animal protein up to 2 percent, and preferably from about 0.1 percent to about 0.5 percent of the cleanser, laneth-10 acetate up to about 10 percent, preferably from about 1 percent to about 3 percent of the cleanser and sorbitan sesquioleate up to about 5 percent, preferably from about 1 percent to about 3 percent of the cleanser, a thickener such as cellulose gum, hydroxy ethyl cellulose, Irish moss, tragacanth and other mucilages, and alkali metal salts of polyacrylic acid up to about 3 percent and preferably from about 1 percent to about 3 percent of the cleanser, a solubilizing agent for the various constituents in the liquid carrier such as propylene glycol and ethylene glycol, these materials being particularly desirable constituents and being present in an amount between about 5 percent and about 25 percent, desirably between about 4 percent and about 6 percent of the cleanser; a preservative such as methyl paraben and propyl paraben, the methyl paraben being present in an amount from about 0.10 percent to about 0.5 percent of the cleanser, desirably from about 0.10 percent to about 0.20 percent by weight of the cleanser, the propyl paraben being present in an amount of from about 0.04 percent to about 0.10 percent, desirably from about 0.04 percent to about 0.06 percent of the cleanser, and a fragrance, typically up to 0.5 percent of the cleanser and desirably from about 0.1 percent to about 0.3 percent of the cleanser. All percentages mentioned are by weight.

DESCRIPTION OF THE PREFERRED EMBODIMENT

As mentioned above, certain components of the nail cleanser necessarily are present, others are optional. The necessary components are a first chelating agent which is a relatively active one, its activity being in comparison to the activity of a second chelating agent which is the second necessary ingredient of the nail cleanser formulation. The third necessary ingredient is a liquid carrier for the first chelating agent and for the second chelating agent. The second chelating agent also functions as a solubilizing agent for various constituents of the nail cleanser.

The optional ingredients are ingredients which are conventionally employed in many other cosmetic formulations for well known functions. These include: one or more mild abrasives, one or more texturizing agents, one or more thickeners, one or more solubilizing agents in addition to the second chelating agent, oen or more preservatives and one or more fragrances.

For the first chelating agent the material of choice is ethylene diamine tetraacetic acid and in particular an alkali metal salt thereof. Other compounds that can be used for the first chelating agent are: phytol, phytic acid, nitrilo-triacetic acid, diethylene triamino pentaacetic acid, sodium tripolyphosphates, sodium metaphosphate, sodium hexamethaphosphate, trisodiumphosphate and ethylene diamino tetraacetic acid. The preferred second ingredient, i.e. the milder chelating agent is urea. Other milder chelating agents which can be used in place of the urea are: allantoin, d-penthenol, aloe vera extract and urea precursors.

The third and last necessary ingredient is a liquid carrier which will solvate or disperse the sundry ingredients of the nail cleanser. The preferred carrier is water since it will perform the function required and is the least costly. In place of or in addition to water, liquid alcohols or acetone can be used.

Insofar as the optional constituents are concerned they constitute the following:

A mild abrasive such as silica, diatomaceous earth and talc.

A texturizing material such as a hydrolized animal protein, laneth-10 acetate and sorbitan sesquioleate.

A thickener such as cellulose gum, hydroxy ethyl cellulose, Irish moss, tragacanth, mucilage and alkali salts of polyacrylic acid.

A solubilizing agent such as propylene glycol and ethylene glycol.

A preservative such as methyl paraben and propyl paraben.

A fragrance.

The preferred optional materials that are employed are silica, hydrolized animal protein, laneth-10 acetate, sorbitan sesquioleate, cellulose gum, glycol, methyl paraben, propyl paraben and a fragrance. In addition it is desirable also to include a small amount of acetone to assist in solubilization.

Set forth below is a preferred formulation for a nail cleanser embodying the invention.

| INGREDIENTS | PERCENTAGE BY WEIGHT OF NAIL CLEANSER |
|---|---|
| Water | 76.05 |
| Disodium EDTA | 2.00 |
| Silica | 1.50 |
| Hydrolyzed Animal Protein | 0.10 |
| Laneth-10 Acetate | 2.00 |
| Acetone | 4.50 |
| Sorbitan Sesquioleate | 1.50 |
| Cellulose Gum | 2.00 |
| Urea | 5.00 |
| Propylene Glycol | 5.00 |
| Methyl Paraben | 0.10 |
| Propyl Paraben | 0.05 |

It will be understood that the invention is not restricted to the particular compounds listed above inasmuch, as mentioned previously, different ingredients may be substituted for the ones listed; moreover the formulation can be varied considerably and to indicate the range of variations there are set forth below the ideal range by weight and the maximum range by weight for each of the mentioned ingredients.

| INGREDIENTS | MAXIMUM RANGE BY WEIGHT OF NAIL CLEANSER | IDEAL RANGE BY WEIGHT |
|---|---|---|
| Water | 40-80% | 70-80% |
| Disodium EDTA | 1-30% | 1-3% |
| Silica | 0-5% | 1-3% |
| Hydrolyzed Animal Protein | 0-2% | 0.10-0.50% |
| Laneth-10 Acetate | 0-10% | 1-3% |
| Acetone | 0-20% | 4-6% |
| Sorbitan Sesquioleate | 0-5% | 1-3% |
| Cellulose Gum | 0-3% | 1-3% |

-continued

| INGREDIENTS | MAXIMUM RANGE BY WEIGHT OF NAIL CLEANSER | IDEAL RANGE BY WEIGHT |
|---|---|---|
| Urea | 1-30% | 4-6% |
| Propylene Glycol | 5-25% | 4-6% |
| Methyl Paraben | 0.10-0.50% | 0.10-0.20% |
| Propyl Paraben | 0.03-0.10% | 0.04-0.06% |
| Fragrance | 0.0-0.5% | 0.1-0.3% |

The pH of the nail cleanser should range between about 6 and about 8 and preferably is substantially neutral, that is to say 7.

The nail cleanser is used simply by applying it to a nail, after the removal of nail polish if present, leaving the cleanser on for a short period, for example about ten seconds to about one half minute, and wiping it off with a rag. It is not necessary to clean off any residue. The small amount of acetone in the cleanser will remove any trace of nail polish that is present.

The viscosity of the nail cleanser can vary quite widely. The only critical factor is that it be sufficient viscous to remain on the nail for a time sufficient to remove the stain, such time having been indicated above.

A typical satisfactory viscosity is 11,000 cps in which form it is a cream.

A study performed on a 100 subjects showed generally excellent results. In the study the preferred nail cleanser formulation was used. It was applied to the nails with a brush after removal of nail polish and left on between about a quarter to half a minute. The nails of people of various ages were cleaned in the aforesaid manner. All the nails of each subject were thus treated. In some instances the nail cleanser was applied more than once. Set forth below are the results of the study:

| SUBJECT NUMBER | AGE | TYPE OF STAIN | HOW MANY APPLICATIONS | RESULTS |
|---|---|---|---|---|
| 1 | 53 | Nail Pigment(Yellow stain) | 4 | Excellent |
| 2 | 52 | Nail Pigment(Yellow stain) | 2 | Excellent |
| 3 | 52 | Nail Pigment(Yellow stain) | 2 | Excellent |
| 4 | 49 | Shoe polish | 4 | Excellent |
| 5 | 37 | Nail pigment(Yellow stain) | 1 | Excellent |
| 6 | 43 | Tobacco stain | 1 | Excellent |
| 7 | 39 | Nail pigment(Yellow stain) | 2 | Excellent |
| 8 | 40 | Nail pigment(yellow stain) | 2 | Excellent |
| 9 | 34 | Nail pigment(yellow stain) | 1 | Excellent |
| 10 | 34 | Nail pigment(yellow stain) | 4 | Excellent |
| 11 | 34 | Nail pigment(yellow stain) | 2 | Excellent |
| 12 | 34 | Nail pigment(yellow stain) | 1 | Excellent |
| 13 | 38 | Nail pigment(yellow stain) | 1 | Excellent |
| 14 | 31 | Nail pigment(yellow stain) | 3 | Excellent |
| 15 | 31 | Nail pigment(yellow stain) | 2 | Excellent |
| 16 | 34 | Tobacco stain | 1 | Excellent |
| 17 | 30 | Nail pigment(yellow stain) | 2 | Excellent |
| 18 | 30 | Nail pigment(tobacco stain) | 1 | Excellent |
| 19 | 39 | Tobacco stain/shoe polish | 2 | Excellent |
| 20 | 40 | Tobacco stain/shoe polish | 2 | Excellent |
| 21 | 36 | Tobacco stain/furniture polish | 1 | Excellent |
| 22 | 27 | Nail pigment(yellow stain) | 1 | Excellent |
| 23 | 30 | Nail pigment(yellow stain) | 1 | Excellent |
| 24 | 27 | Tobacco stain | 2 | Excellent |
| 25 | 58 | Nail pigment(yellow stain) | 1 | Excellent |
| 26 | 62 | Nail pigment(yellow stain) | 1 | Excellent |
| 27 | 36 | Nail pigment/tobacco stain | 2 | Excellent |
| 28 | 22 | Nail pigment(yellow stain) | 1 | Excellent |
| 29 | 52 | Dye | 1 | Excellent |
| 30 | 62 | Nail stain/tobacco stain | 1 | Excellent |
| 31 | 49 | Iodine/shoe polish/tobacco | 3 | Excellent |
| 32 | 53 | Nail pigment(yellow stain) | 1 | Excellent |
| 33 | 54 | Nail pigment(yellow stain) | 1 | Excellent |
| 34 | 47 | Nail pigment(yellow stain) | 2 | Excellent |
| 35 | 47 | Nail pigment(yellow stain) | 1 | Excellent |
| 36 | 55 | Nail pigment(tobacco stain | 3 | Excellent |
| 37 | 47 | Other | 1 | Excellent |
| 38 | 55 | Nail pigment/tobacco stain | 4 | Excellent |
| 39 | 50 | Shoe polish | 1 | Excellent |
| 40 | 38 | Nail pigment/tobacco stain | 4 | Excellent |
| 41 | 14 | Nail pigment(yellow stain) | 1 | Excellent |
| 42 | 35 | Nail pigment/tobacco stain | 1 | Excellent |
| 43 | 33 | Nail pigment/tobacco stain | 2 | Excellent |
| 44 | 36 | Nail pigment(yellow stain) | 2 | Excellent |
| 45 | 46 | Nail pigment(yellow stain) | 2 | Excellent |
| 46 | 66 | Tobacco stain | 1 | Excellent |
| 47 | 37 | Furniture stain | 1 | Excellent |
| 48 | 21 | Hair dye | 2 | Excellent |
| 49 | 30 | Nail pigment(yellow stain) | 1 | Excellent |
| 50 | 28 | Nail pigment/tobacco stain | 1 | Excellent |
| 51 | 41 | Shoe polish | 1 | Excellent |
| 52 | 51 | Nail pigment(yellow stain) | 2 | Excellent |
| 53 | 43 | Nail pigment(yellow stain) | 1 | Excellent |
| 54 | 39 | Nail pigment(yellow stain) | 1 | Excellent |
| 55 | 48 | Nail pigment(yellow stain) | 2 | Excellent |
| 56 | 55 | Nail pigment(yellow stain) | 2 | Excellent |

-continued

| SUBJECT NUMBER | AGE | TYPE OF STAIN | HOW MANY APPLICATIONS | RESULTS |
|---|---|---|---|---|
| 57 | 53 | Nail pigment(yellow stain) | 1 | Excellent |
| 58 | 53 | Nail pigment(yellow stain) | 1 | Excellent |
| 59 | 33 | Nail pigment(yellow stain) | 2 | Excellent |
| 60 | 47 | Nail pigment(yellow stain) | 1 | Excellent |
| 61 | 52 | Nail pigment(yellow stain) | 1 | Excellent |
| 62 | 57 | Nail pigmen/tobacco stain | 4 | Excellent |
| 63 | 32 | Tobacco stain | 1 | Excellent |
| 64 | 34 | Tobacco stain | 1 | Excellent |
| 65 | 26 | Nail pigment/tobacco stain | 2 | Excellent |
| 66 | 24 | Nail pigment(yellow stain) | 1 | Excellent |
| 67 | 35 | Nail pigment(yellow stain) | 4 | Excellent |
| 68 | 29 | Nail pigment(yellow stain) | 1 | Excellent |
| 69 | 35 | Tobacco stain | 1 | Excellent |
| 70 | 37 | Nail pigment(yellow stain) | 2 | Excellent |
| 71 | 45 | Nail pigment(yellow stain) | 4 | Good-slight yellow tinge remained on 4 fingers |
| 72 | 34 | Nail pigment/tobacco stain | 3 | Excellent |
| 73 | 47 | Nail pigment(yellow stain) | 4 | Good-slight yellow tinge remained on 5 fingers |
| 74 | 56 | Nail pigment(yellow stain) | 1 | Excellent |
| 75 | 59 | Nail pigment(yellow stain) | 1 | Excellent |
| 76 | 44 | Nail pigment(yellow stain) | 1 | Excellent |
| 77 | 50 | Nail pigment(yellow stain) | 1 | Excellent |
| 78 | 39 | Nail pigment(yellow stain) | 1 | Excellent |
| 79 | 53 | Tobacco stain | 2 | Excellent |
| 80 | 31 | Nail pigment(yellow stain) | 1 | Excellent |
| 81 | 36 | Nail pigment(yellow stain) | 1 | Excellent |
| 82 | 14 | Nail pigment(yellow stain) | 1 | Excellent |
| 83 | 54 | Nail pigment(yellow stain) | 5 | Good-slight stain remained on all fingers |
| 84 | 18 | Nail pigment/tobacco stain | 1 | Excellent |
| 85 | 22 | Nail pigment/tobacco stain | 1 | Excellent |
| 86 | 47 | Tobacco stain | 2 | Excellent |
| 87 | 57 | Nail pigment(yellow stain) | 1 | Excellent |
| 88 | 29 | Nail pigment(yellow stain) | 1 | Excellent |
| 89 | 39 | Nail pigment(yellow stain) | 1 | Excellent |
| 90 | 37 | Nail pigment(yellow stain) | 1 | Excellent |
| 91 | 24 | Nail pigment(yellow stain) | 1 | Excellent |
| 92 | 21 | Nail pigment/tobacco stain | 1 | Excellent |
| 93 | 27 | Tobacco stain | 1 | Excellent |
| 94 | 25 | Nail pigment(yellow stain) | 1 | Excellent |
| 95 | 22 | Nail pigment(yellow stain) | 1 | Excellent |
| 96 | 25 | Tobacco stain | 1 | Excellent |
| 97 | 26 | Nail pigment(yellow stain) | 1 | Excellent |
| 98 | 24 | Nail pigment(yellow stain) | 1 | Excellent |
| 99 | 28 | Nail pigment(yellow stain) | 1 | Excellent |
| 100 | 23 | Tobacco stain | 1 | Excellent |

It thus will be seen that there has been provided a nail cleanser which achieves the various objects of the invention and is well adapted to meet the conditions of practical use.

As various possible embodiments might be made of the above invention, and as various changes might be made in the embodiment above set forth it is to be understood that all matter herein described is to be interpreted as illustrative and not in a limited sense.

I claim:

1. A nail cleanser for application to human nails to remove stains therefrom, said cleanser constituting a composition essentially comprising as necessary ingredients a first chelating agent, a second chelating agent and a liquid carrier which will solvate or disperse said first and said second chelating agents, said first chelating agent being more effective than said second chelating agent, the second chelating agent also being a solubilizing agent, said first chelating agent being selected from the group consisting of ethylene diamine tetraacetic acid and alkali metal salts thereof, phytol, phytic acid, nitrilo-triacetic acid, diethylene triamino pentacetic acid, sodium tripolyphosphates, sodium metaphosphate, sodium hexamethaphosphate, trisodium phosphate and ethylene diaminotetraacetic acid, and the second chelating agent being selected from the group consisting of urea, allantoin, penthenol and aloe vera extract and urea precursors.

2. A nail cleanser as set forth in claim 1 wherein the first chelating agent being present in an amount of from about 1 percent to about 3 percent by weight of the liquid cleanser, the second chelating agent being present in an amount of from about 4 percent to about 6 percent by weight of the nail cleanser, and the liquid carrier being present in an amount of from about 70 percent to about 80 percent of the liquid cleanser, said liquid cleanser further including optional ingredients making up the balance of the weight and comprising one or more mild abrasives, a one or more texturizing agents, one or more thickener, one or more solubilizing agents, one or more preservatives and one or more fragrances.

3. A nail cleanser as set forth in claim 2 wherein the mild abrasive is selected from the group consisting of silica, diatomaceous earth and talc, wherein the texturizing agent is selected from the group consisting of hydrolized animal protein, laneth 10-acetate and sorbitan sesquioleate, wherein the thickener is selected from the group consisting of cellulose gum, hydroxy ethyl cellulose, Irish moss, tragacanth, mucilage, and alkali metal salts of polyacrylic acid, wherein the solubilizing agent is selected from the group consisting of propylene glycol and ethylene glycol and wherein the preservative is selected from the group consisting of methyl paraben and ethyl paraben.

4. A nail cleanser as set forth in claim 3 wherein a mild abrasive is present in an amount up to about 5 percent of the weight of the cleanser, a texturizing agent is present in an amount up to about 10 percent by weight of the cleanser, a thickener is present in an amount up to about 3 percent by weight of the cleanser, a solubilizing agent is present in an amount up to about 25 percent by weight of the cleanser, a preservative is present in an amount up to about 0.6 percent by weight of the cleanser and a fragrance is present in an amount up to about 0.5 percent by weight of the cleanser.

5. A nail cleanser as set forth in claim 4 having the following formulation:

| INGREDIENTS | MAXIMUM RANGE BY WEIGHT OF NAIL CLEANSER |
| --- | --- |
| Water | 40-80% |
| Disodium EDTA | 1-30% |
| Silica | 0-5% |
| Hydrolyzed Animal Protein | 0-2% |
| Laneth-10 Acetate | 0-10% |
| Acetone | 0-20% |
| Sorbitan Sesquioleate | 0-5% |
| Cellulose Gum | 0-3% |
| Urea | 1-30% |
| Propylene Glycol | 5-25% |
| Methyl Paraben | 0.10-0.50% |
| Propyl Paraben | 0.03-0.10% |
| Fragrance | 0.0-0.5% |

6. A nail cleanser as set forth in claim 4 having the following formulation:

| INGREDIENTS | IDEAL RANGE BY WEIGHT |
| --- | --- |
| Water | 70-80% |
| Disodium EDTA | 1-3% |
| Silica | 1-3% |
| Hydrolyzed Animal Protein | 0.10-0.50% |
| Laneth-10 Acetate | 1-3% |
| Acetone | 4-6% |
| Sorbitan Sesquioleate | 1-3% |
| Cellulose Gum | 1-3% |
| Urea | 4-6% |
| Propylene Glycol | 4-6% |
| Methyl Paraben | 0.10-0.20% |
| Propyl Paraben | 0.04-0.06% |
| Fragrance | 0.1-0.3% |

7. A nail cleanser as set forth in claim 4 having the following formulations:

| INGREDIENTS | PERCENTAGE BY WEIGHT OF THE NAIL CLEANSER |
| --- | --- |
| Water | 76.05 |
| Disodium EDTA | 2.00 |
| Silica | 1.50 |
| Hydrolyzed Animal Protein | 0.10 |
| Laneth-10 Acetate | 2.00 |
| Acetone | 4.50 |
| Sorbitan Sesquioleate | 1.50 |
| Cellulose Gum | 2.00 |
| Urea | 5.00 |
| Propylene Glycol | 5.00 |
| Methyl Paraben | 0.10 |
| Propyl Paraben | 0.05 |

* * * * *